(12) United States Patent
Ogi et al.

(10) Patent No.: US 11,125,716 B2
(45) Date of Patent: Sep. 21, 2021

(54) POTENTIAL MEASUREMENT DEVICE

(71) Applicant: SONY SEMICONDUCTOR SOLUTIONS CORPORATION, Kanagawa (JP)

(72) Inventors: Jun Ogi, Kanagawa (JP); Yusuke Oike, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 286 days.

(21) Appl. No.: 15/761,693

(22) PCT Filed: Aug. 9, 2016

(86) PCT No.: PCT/JP2016/073478
§ 371 (c)(1),
(2) Date: Mar. 20, 2018

(87) PCT Pub. No.: WO2017/061171
PCT Pub. Date: Apr. 13, 2017

(65) Prior Publication Data
US 2018/0348161 A1    Dec. 6, 2018

(30) Foreign Application Priority Data

Oct. 9, 2015  (JP) .............................. JP2015-201155

(51) Int. Cl.
*G01N 27/416*    (2006.01)
*G01N 27/30*     (2006.01)
(Continued)

(52) U.S. Cl.
CPC ........... *G01N 27/416* (2013.01); *G01N 27/27* (2013.01); *G01N 27/30* (2013.01); *G01N 27/301* (2013.01);
(Continued)

(58) Field of Classification Search
CPC ...... G01N 27/416; G01N 27/27; G01N 27/30; G01N 27/301; G01N 27/403;
(Continued)

(56) References Cited

U.S. PATENT DOCUMENTS 6,714,666 B1 *  3/2004  Morimura ............ G06K 9/0002
                                                            340/5.52
2009/0004685 A1 *  1/2009  Huys .................. G01N 33/5008
                                                            435/29
(Continued)

FOREIGN PATENT DOCUMENTS

AU    1466301 A    5/2001
CN    1809628 A    7/2006
(Continued)

OTHER PUBLICATIONS

Berdondini et al., High-Density Microelectrode Arrays for Electrophysiological Activity Imaging of Neuronal Networks, ICECS 2001, 8th IEEE international conference on electronics, circuits and systems (Cat. No. 01EX483), vol. 3, IEEE (2001) (Year: 2001).*

(Continued)

*Primary Examiner* — James Lin
*Assistant Examiner* — Vivian A Tran
(74) *Attorney, Agent, or Firm* — Chip Law Group

(57) ABSTRACT

A potential measurement device includes a plurality of read-out electrodes arranged in an array shape and that detects a potential at a potential generation point generated due to a chemical change, and a reference electrode that detects a reference potential. The reference electrode is arranged within the array of the read-out electrodes. With this configuration, a low-noise potential measurement device in which noise superimposed on a wire from each of the read-out electrodes to an amplifier and noise superim- (Continued)

posed on a wire from the reference electrode to the amplifier, i.e., wiring noise, can be reduced is achieved.

8 Claims, 7 Drawing Sheets

(51) Int. Cl.
*G01N 27/403* (2006.01)
*G01N 27/27* (2006.01)
*G01N 33/483* (2006.01)
*G01N 33/487* (2006.01)

(52) U.S. Cl.
CPC ....... *G01N 27/403* (2013.01); *G01N 33/4836* (2013.01); *G01N 33/48728* (2013.01)

(58) Field of Classification Search
CPC .............. G01N 33/483; G01N 33/4833; G01N 33/4836; G01N 33/48728
See application file for complete search history.

(56) References Cited

U.S. PATENT DOCUMENTS

| | | | |
|---|---|---|---|
| 2010/0038247 | A1 | 2/2010 | Zimmermann et al. |
| 2010/0133122 | A1 | 6/2010 | Ozaki et al. |
| 2010/0301398 | A1* | 12/2010 | Rothberg ............ G01N 27/4145 257/253 |
| 2014/0346058 | A1* | 11/2014 | Robitzki ............. G01N 27/327 205/777.5 |

FOREIGN PATENT DOCUMENTS

| | | |
|---|---|---|
| EP | 1230539 A1 | 8/2002 |
| EP | 2581742 A1 | 4/2013 |
| JP | 2000-041671 A | 2/2000 |
| JP | 2002-031617 A | 1/2002 |
| JP | 2003-513275 A | 4/2003 |
| JP | 2003-287513 A | 10/2003 |
| JP | 3801617 B2 | 7/2006 |
| JP | 2013-094168 A | 5/2013 |
| JP | 2014-533933 A | 12/2014 |
| KR | 10-2014-0084139 A | 7/2014 |
| WO | 2001/033207 A1 | 5/2001 |
| WO | WO-0133207 A1 * | 5/2001 ......... G01N 33/4836 |
| WO | 2002/055653 A1 | 7/2002 |
| WO | 2013/053513 A1 | 4/2013 |

OTHER PUBLICATIONS

International Search Report and Written Opinion of PCT Application No. PCT/JP2016/073478, dated Oct. 4, 2016, 10 pages.
Berdondini, et al., "Active Pixel Sensor Array for High Spatio-Temporal Resolution Electrophysiological Recordings From Single Cell to Large Scale Neuronal Networks", The Royal Society of Chemistry 2009, Lab Chip, 2009, DOI: 10.1039/b907394a, vol. 9, No. 8, Sep. 21, 2009, pp. 2644-2651.
Frey, et al., "Switch-Matrix-Based High-Density Microelectrode Array in CMOS Technology", IEEE Journal of Solid-State Circuits, vol. 45, No. 2, Feb. 2010, pp. 467-482.
Obien, et al., "Revealing Neuronal Function Through Microelectrode Array Recordings", vol. 8, Article 423, Jan. 2015, 30 pages.
Berdondini, et al., "Active Pixel Sensor Array for High Spatio-Temporal Resolution Electrophysiological Recordings from Single Cell to Large Scale Neuronal Networks", Lab Chip, vol. 9, 2009, pp. 2644-2651.
Frey, et al., "Switch-Matrix-Based High-Density Microelectrode Array in CMOS Technology", IEEE Journal of Solid-State Circuits, vol. 45, Issue 2, Feb. 2010, pp. 467-482.
Obien, et al., "Revealing Neuronal Function Through Microelectrode Array Recordings", Frontiers in Neuroscience, vol. 8, Jan. 2015, 30 pages.
Notice of Allowance for JP Patent Application No. 2017-544399, dated Mar. 2, 2021, 3 pages of Notice of Allowance and 2 pages of English Translation.

* cited by examiner

POTENTIAL MEASUREMENT DEVICE

CROSS REFERENCE TO RELATED APPLICATIONS

This application is a U.S. National Phase of International Patent Application No. PCT/JP2016/073478 filed on Aug. 9, 2016, which claims priority benefit of Japanese Patent Application No. JP 2015-201155 filed in the Japan Patent Office on Oct. 9, 2015. Each of the above-referenced applications is hereby incorporated herein by reference in its entirety.

TECHNICAL FIELD

The present disclosure relates to a potential measurement device.

BACKGROUND ART

A potential measurement device has a configuration in which fine read-out electrodes are arranged in an array shape to electrochemically measure a potential generated due to a chemical change of a solution placed on the read-out electrodes. For example, there is a potential measurement device having a configuration in which living cells are placed on read-out electrodes filled with a culture solution, to thereby measure an action potential generated by living cells (e.g., see Patent Document 1). In particular, a potential measurement device having a configuration in which electrodes, amplifiers, A/D converters, and the like are integrated on one semiconductor substrate (chip) by using a complementary metal oxide semiconductor (CMOS) integrated circuit technique, to thereby measure potentials at multiple points at the same time has recently been attracting attention.

Potential measurement devices using the CMOS integrated circuit technique are roughly divided into two types. Specifically, the potential measurement devices are divided into a potential measurement device (e.g., see Non-Patent Document 1) that measures a potential by dynamically reconnecting wires of respective read-out electrodes and connecting the read-out electrodes to an independent amplifier, and a potential measurement device (e.g., see Non-Patent Document 2) having a configuration in which read-out electrodes and amplifiers are provided in one-to-one correspondence.

The former potential measurement device has an advantage that the size of each amplifier can be increased to reduce noise. However, the number of amplifiers is limited, and the number of simultaneous measurement points is also limited. In the latter potential measurement device, the individual amplifiers are simultaneously operated, which leads to an increase in the number of simultaneous measurement points. However, it is pointed out that, in the latter potential measurement device, there is a trade-off relationship between the number of simultaneous measurement points and noise, specifically, for example, the size of each amplifier is small, but noise is large (e.g., see Non-Patent Document 3).

These potential measurement devices are different in regard to the position of each read-out electrode, but have basically the same potential measurement principle. Specifically, the potential measurement devices are configured to measure a local potential change by taking the potential difference between a potential detected by each of reference electrodes arranged in a liquid solvent placed far from cells and a potential detected by each of read-out electrodes arranged near the cells.

CITATION LIST

Patent Document

Patent Document 1: Japanese Patent Application Laid-Open No. 2002-31617
Non-Patent Document 1: IEEE Journal of Solid State Circuits Vol. 45 (2010) No. 2 pp. 467-482
Non-Patent Document 2: Las on a Chip Vol. 9 (2009) pp. 2647-2651
Non-Patent Document 3: Frontiers in Neuro Science Vol. 8 (2015) Article 423

SUMMARY OF THE INVENTION

Problems to be Solved by the Invention

As described above, in the potential measurement device in which the number of simultaneous measurement points is increased by using the CMOS integrated circuit technique, there is a trade-off relationship between the number of simultaneous measurement points and noise. A major reason for this is that the size of each amplifier, which is a largest noise source, is limited. However, noise sources other than the amplifier are also present, and thus it is also important to reduce noise from these noise sources. Wiring noise is one example of noise sources other than the amplifier.

In the potential measurement device, a differential amplifier is used to take the potential difference between the potential generated by each of the reference electrodes in the solution placed far from the action potential generation point and the potential generated by each of the read-out electrodes arranged in the vicinity of the action potential generation point, and two input terminals of the amplifier are connected to the respective electrodes with wires, thereby taking the potential difference. In this manner, environmental noise can be canceled by taking the potential difference between the potential generated by each of the reference electrodes and the potential generated by each of the read-out electrodes.

However, in the potential measurements devices using the CMOS integrated circuit technique, particularly, in the potential measurement device having a configuration in which an amplifier is provided for each of the electrodes, the read-out electrode is arranged near the amplifier in many cases and the reference electrode is arranged at a position far from the position of the amplifier, specifically, arranged at a position where potential variations are small. Thus, if the position of the read-out electrode and the position of the reference electrode are at greatly different distances from the position of the amplifier, noise superimposed on a wire from the read-out electrode to the amplifier is different from noise superimposed on a wire from the reference electrode to the amplifier. As a result, noise (wiring noise) superimposed on both wires cannot be canceled, which leads to an increase in noise included in a measuring output.

Therefore, an object of the present disclosure is to reduce the wiring noise and provide a low-noise potential measurement device.

Solutions to Problems

To attain the above-mentioned object, a potential measurement device according to the present disclosure includes:

a plurality of read-out electrodes arranged in an array shape and configured to detect a potential at an action potential generation point generated due to a chemical change;

a reference electrode configured to detect a reference potential; and an amplification unit configured to obtain a potential difference between a detection potential detected by each of the read-out electrodes and a detection potential detected by the reference electrode, in which the reference electrode is arranged within the array of the read-out electrodes.

In the potential measurement device having the configuration described above, the reference electrode is arranged within the array of the read-out electrodes, so that the reference electrode is arranged in the vicinity of each of the read-out electrodes, and the position of each of the read-out electrodes and the position of the reference electrode can be located at an equal distance from the position of the amplifier. With this configuration, a wire for connecting each of the read-out electrodes and the amplification unit and a wire for connecting the reference electrode and the amplification unit have an approximately electrically equivalent wiring capacitance and capacitance with environment. Accordingly, noise included in an output from the amplifier when the difference is taken is reduced. As a result, wiring noise can be reduced.

Effects of the Invention

According to the present disclosure, it is possible to reduce wiring noise and provide a low-noise potential measurement device.

Note that advantageous effects are not necessarily limited to those described herein, and any one of the advantageous effects described herein may be obtained. Further, the advantageous effects described herein are merely examples, and the present disclosure is not limited to these advantageous effects, and additional advantageous effects may be obtained.

MODE FOR CARRYING OUT THE INVENTION

Figure 1:
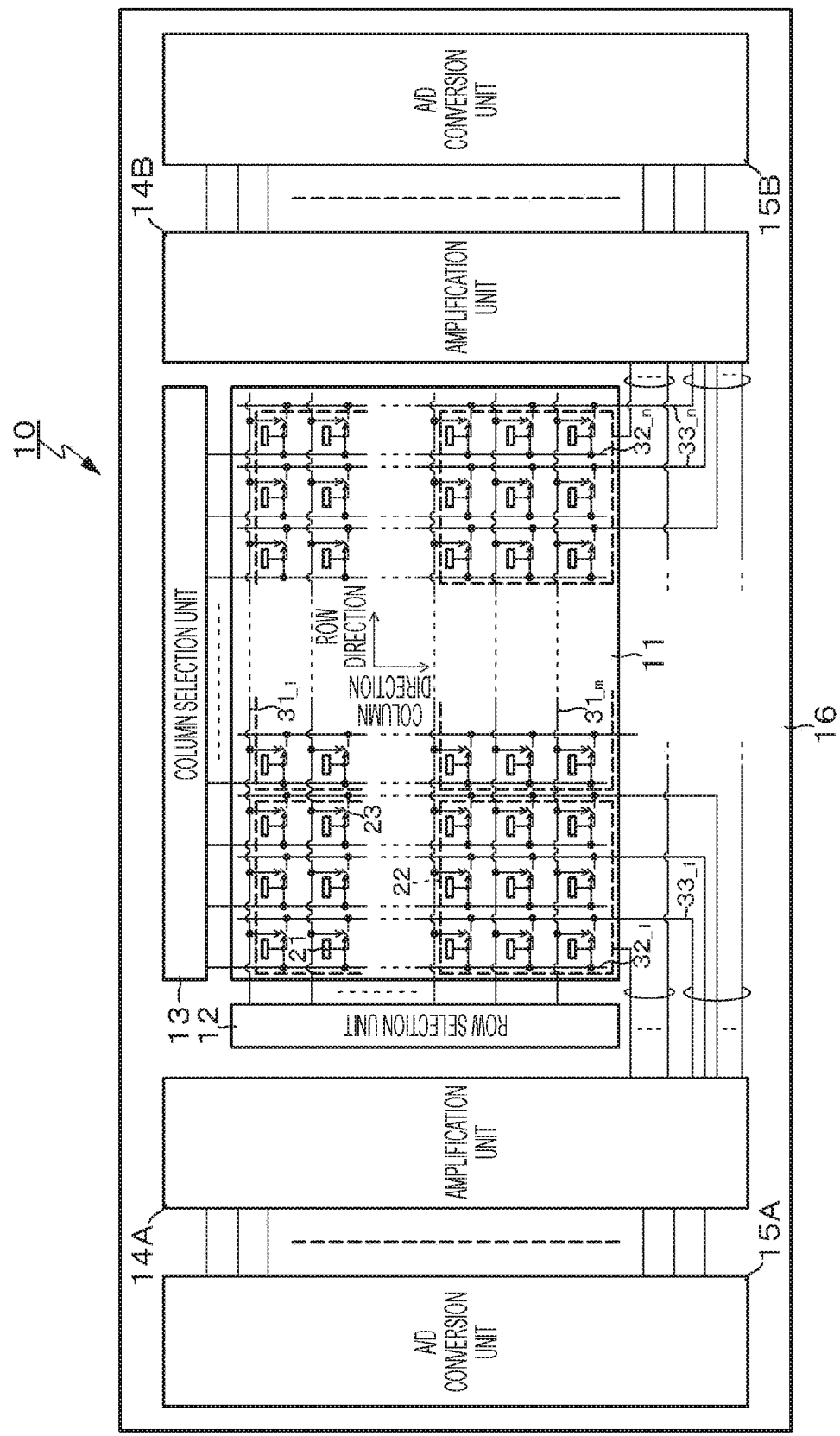
FIG. 1 is a configuration diagram schematically illustrating a configuration of a potential measurement device according to Embodiment 1.

Modes for carrying out a technique according to the present disclosure (hereinafter referred to as "embodiments") will be described in detail below with reference to the drawings. The technique according to the present disclosure is not limited to embodiments, and various values and the like in the embodiments are illustrated by way of example. In the following description, the same elements or elements having the same functions are denoted by the same reference numerals, and repeated descriptions of the elements are omitted. Note that the following description is made in the following order.

1. Description of an overall configuration of a potential measurement device according to the present disclosure
2. A potential measurement device according to one embodiment of the present disclosure
2-1. Embodiment 1 (an example in which an amplifier is commonly provided for a plurality of read-out electrodes)
2-2. Embodiment 2 (a modified example of Embodiment 1)
2-3. Embodiment 3 (a modified example of Embodiment 1)
2-4. Embodiment 4 (a modified example of Embodiment 1 and Embodiment 3)
2-5. Embodiment 5 (a modified example of Embodiment 1)

Description of an Overall Configuration of a Potential Measurement Device According to the Present Disclosure A potential measurement device according to the present disclosure may have a configuration in which read-out electrodes, reference electrodes, and amplifiers are integrated on one semiconductor substrate. In addition, the potential measurement device may have a mode in which an electrode size of each reference electrode is larger than an electrode size of each read-out electrode, and the read-out electrodes each have an electrode size substantially equal to the size of an action potential generation point. At this time, each reference electrode may include a plurality of opening portions within a plane of each of the reference electrode, and the read-out electrodes may be arranged in such a manner that the read-out electrodes are respectively located within the opening portions of each of the reference electrodes.

The potential measurement device according to the present disclosure including a preferable configuration as described above may include an A/D conversion unit which performs A/D conversion of an output from each amplifier and is formed provided on a semiconductor substrate on which the read-out electrodes, the reference electrodes, and the amplifiers are formed. In addition, the amplification unit includes a plurality of differential amplifiers. The plurality of differential amplifiers may be commonly provided for the plurality of read-out electrodes, or may be respectively provided for the plurality of read-out electrodes.

Further, the potential measurement device according to the present disclosure including the preferable configuration described above may include a first electrode having a relatively large electrode size and a second electrode having a relatively small electrode size. Further, the potential measurement device may be configured to be capable of switching between a case where the first electrode is used as each of the reference electrodes and the second electrode is used as each of the read-out electrodes and a case where the first electrode is used as each of the read-out electrodes and the second electrode is used as each of the reference electrodes. In this case, a detection potential of each of the second electrodes may be set as a detection potential at the action potential generation point, and a plurality of first electrodes may be grouped and an average value of detection potentials of the plurality of first electrodes may be set as the reference potential. Alternatively, a plurality of second electrodes may be grouped, an average of the detection potentials of these electrodes is taken, and the average value may be set as the reference potential, and second electrodes other than the plurality of second electrodes and the first electrode may be grouped and an average value of detection potentials of the second electrodes other than the plurality of second electrodes and the first electrode may be set as a detection potential at the action potential generation point. More alternatively, a large number of fine electrodes may be arranged in an array shape, an average value of detection potentials of several fine electrodes may be set as a detection potential of the second electrode, and an average value of detection potentials of several hundred or more fine electrodes may be set as a detection potential of the first electrode.

Further, in the potential measurement device according to the present disclosure including a preferable configuration as described above, in a case where an electrode size of each of the read-out electrodes is larger than the electrode size of each of the reference electrodes, potential conversion capacitances having the same capacitance value may be connected in series between the amplification unit and each of the read-out electrodes and the reference electrodes, and a capacitance value of each of the potential conversion capacitance may be smaller than an electrode-to-solvent capacitance value of each of the read-out electrodes and the reference electrodes.

Further, in the potential measurement device according to the present disclosure including a preferable configuration as described above, an electrode structure of each of the read-out electrodes and the reference electrodes may be a planar structure. Alternatively, an electrode structure of each of the reference electrodes may be a planar structure, and an electrode structure of each of the read-out electrodes may be a three-dimensional structure for increasing the electrode surface area.

A Potential Measurement Device According to one Embodiment of the Present Disclosure A potential measurement device according to this embodiment is a device having a configuration in which a plurality of read-out electrodes arranged in an array shape, reference electrodes, and amplifiers each configured to obtain a potential difference between a detection potential detected by each of the read-out electrodes and a detection potential detected by each of the reference electrodes are preferably integrated on one semiconductor substrate (semiconductor chip). The plurality of read-out electrodes each detects, by simultaneous measurement, a potential at an action potential generation point generated due to a chemical change. The reference electrodes each detect, as a reference potential, a standard potential used as a criterion in a case where a difference is taken between the reference potential and the potential at the action potential generation point detected by each of the read-out electrodes.

Further, the potential measurement device according to this embodiment is characterized by having a configuration in which each reference electrode is arranged within the array of the read-out electrodes. Thus, the arrangement of the reference electrode within the array of the read-out electrodes enables the reference electrode to be arranged near each read-out electrode and also enables setting of the position of the read-out electrode and the position of the reference electrode to be located at an equal distance from the position of the corresponding amplifier. Thus, a wire for connecting each read-out electrode and the corresponding amplification unit and a wire for connecting each reference electrode and the corresponding amplification unit have an approximately electrically equivalent wiring capacitance and capacitance with environment, and thus noise superimposed on one of these wires can be made equal to noise superimposed on the other one of these wires. Accordingly, noise included in an output from the amplifier when the difference is taken is reduced. As a result, wiring noise can be reduced.

Incidentally, in general, read-out electrodes are arranged in the vicinity of an action potential generation point where an action potential of a living cell (hereinafter also referred to simply as a "cell") is generated, and each reference electrode is arranged at a position far from the read-out electrodes so as not to be affected by the action potential, thereby obtaining the potential difference between the electrodes. On the other hand, in the potential measurement device according to this embodiment, as described below, electrodes having different sizes and different surface areas are used for each of the read-out electrodes and the reference electrodes, and the potential difference can be taken using the difference in potential measurement position and the difference in capacitance, thereby enabling arrangement of each reference electrode in the vicinity of the read-out electrodes.

The action potential of a cell is obtained by reading out a variation of ions that are changed by cell activities. Specifically, a change in the number of ions locally generated causes a change in the number of ions of an electrode unit, i.e., the amount of electric change, and a variation in the electric charge is converted into a potential difference to be read out. The potential difference is a value obtained by dividing the variation in electric charge by the capacitance of each electrode.

A change in the amount of electric charge of each electrode is determined by a variation of ions transmitted from the action potential generation point. However, since a solvent serves as a resistor, a variation of ions decreases in reverse proportion to the distance from the action potential generation point. Accordingly, in a case where the size of the action potential generation point is relatively small and the number of action potential generation points is small, a variation of electric charge does not increase in proportion to an increase in the electrode size. On the other hand, the capacitance of each electrode increases in proportion to the electrode size, so that a potential variation decreases in proportion to the electrode size.

In the potential measurement device according to this embodiment, the size of each of the read-out electrodes is reduced as much as possible using the above-mentioned properties, and a large electrode arranged around the read-out electrodes is used as the reference electrode. With this configuration, even in a state where the reference electrode is arranged in the vicinity of the read-out electrodes, the potential difference between each read-out electrode and the reference electrode can be measured.

Alternatively, in a situation where a large number of action potential generation sources are dispersed, in the case of taking the entire potential change, the amount of input electric charge increases as the area of the electrode increases, and a potential change also increases. By using this property, the potential difference between each read-out electrode and the reference electrode can also be measured by using a large electrode as each read-out electrode and using a small electrode located in the vicinity of the read-out electrode as the reference electrode.

Specific embodiments of the potential measurement device according to this embodiment will be described below.

Embodiment 1

FIG. 1 is a configuration diagram schematically illustrating a configuration of a potential measurement device according to Embodiment 1. A potential measurement device 10 according to this embodiment has a configuration in which an electrode unit 11 which is created using a CMOS integrated circuit technique, a row selection unit 12, a column selection unit 13, amplification units 14A and 14B, and A/D conversion units 15A and 15B are integrated on one semiconductor substrate (semiconductor chip) 16. Herein, the configuration in which the amplification unit 14A and the A/D conversion unit 15A, and the amplification unit 14B and the A/D conversion unit 15B are respectively arranged at both sides with the electrode unit 11 interposed therebetween is employed. Alternatively, a configuration in which the amplification units and the A/D conversion units are arranged at one side of the electrode unit 11 may be employed.

In the electrode unit 11, m rows and n columns of a plurality of read-out electrodes 21 each configured to detect a potential at an action potential generation point generated due to a chemical change are arranged in an array shape. The read-out electrodes 21 have an electrode size that is, for example, substantially equal to the size of the action potential generation point. Each of reference electrodes 22 configured to detect the reference potential is arranged within the array of the read-out electrodes 21.

Herein, for example, each reference electrode 22 is arranged in such a manner that nine read-out electrodes 21, i.e., three read-out electrodes 21 in the row direction×three read-out electrodes 21 in the column direction, are arranged, and the electrode size of each of the read-out electrodes 21 is smaller than the electrode size of each of the reference electrodes 22. In other words, the electrode size of each of the reference electrodes 22 is larger than the electrode size of each of the read-out electrodes 21. The reference potential detected by each of the reference electrodes 22 is a standard potential used as a criterion when a difference is taken between the reference potential and the potential at the action potential generation point detected by each of the read-out electrodes 21. The electrode structure of each of the read-out electrodes 21 and the reference electrodes 22 is a planar structure.

In the arrangement of m rows and n columns of read-out electrodes 21, row selection lines $31_{\_1}$ to $31_{\_m}$ are wired for each row, and column selection lines $32_{\_1}$ to $32_{\_n}$ and signal read-out lines $33_{\_1}$ to $33_{\_n}$ are wired for each column. One end of each of the row selection lines $31_{\_1}$ to $31_{\_m}$ is connected to an output end in a row corresponding to the row selection unit 12. One end of each of the column selection lines $32_{\_1}$ to $32_{\_n}$ is connected to an output end in a column corresponding to the column selection unit 13.

The read-out electrodes 21 are respectively connected to the signal read-out lines $33_{\_1}$ to $33_{\_n}$ via respective switches 23. FIG. 1 illustrates each switch 23 as one switch, for simplicity of the drawings. However, in practice, each switch 23 includes at least two switches, i.e., a switch for row selection and a switch for column selection. In addition, to correspond to the respective switches, the signal read-out lines $33_{\_1}$ to $33_{\_n}$ each include at least two signal read-out lines.

In each switch 23, for example, the switch for row selection is driven to be turned on (closed) by a row selection signal applied from the row selection unit 12 via the row selection lines $31_{\_1}$ to $31_{\_m}$, and the switch for column selection is driven to be turned on by a column selection signal applied from the column selection unit 13 via the column selection line $32_{\_1}$ to $32_{\_n}$. When the switch for the row selection and the switch for column selection are turned on, the potential detected by the read-out electrodes 21 is output to the signal read-out lines $33_{\_1}$ to $33_{\_n}$ and is transmitted to the amplification units 14A and 14B through the signal read-out lines $33_{\_1}$ to $33_{\_n}$.

Note that the potential read-out system of the read-out electrodes 21 is herein described as a subject, but the potential read-out system of the reference electrodes 22 also has a configuration basically similar to that of the potential read-out system of the read-out electrodes 21. Specifically, in the potential read-out system including the row selection unit 12, the column selection unit 13, the row selection lines $31_{\_1}$ to $31_{\_m}$, the column selection lines $32_{\_1}$ to $32_{\_n}$, and the signal read-out lines $33_{\_1}$ to $33_{\_n}$, two channels of a channel for reading out potentials of the read-out electrodes 21 and a channel for reading out potentials of the reference electrodes 22 are provided.

A detection potential of each of the read-out electrodes 21 read out by the two-channel potential read-out system and a detection potential of each of the reference electrodes 22 read out by the two-channel potential read-out system are supplied to the amplification units 14A and 14B. The amplification units 14A and 14B each include a plurality of differential amplifiers commonly provided for the plurality of read-out electrodes 21, and take a difference between a detection potential (reference potential) of each of the reference electrodes 22 and a detection potential of each of nine read-out electrodes 21 belonging to the reference electrodes 22, for example, for each reference electrode 22. This difference is supplied to the A/D conversion units 15A and 15B. The A/D conversion units 15A and 15B perform A/D conversion of the difference output from the amplification units 14A and 14B, and outputs a digital value corresponding to the potential detected by each of the read-out electrodes 21.

Figure 2A:
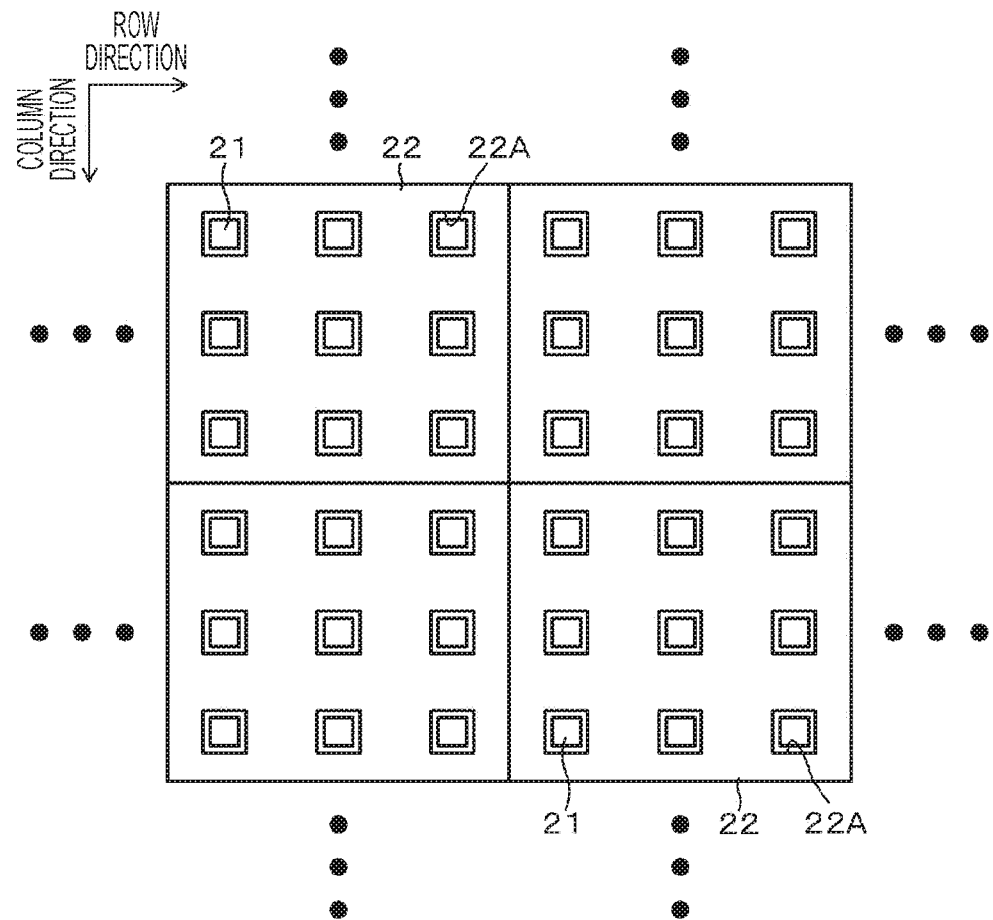
FIG. 2A is a plan view illustrating an example of an electrode layout of reference electrodes each having a square electrode shape and read-out electrodes.

In the potential measurement device 10 according to Embodiment 1 having the configuration described above, each reference electrode 22 is arranged in the vicinity of the read-out electrodes 21, specifically, within the array of the read-out electrodes 21. Further, the size of each of reference electrode 22 is larger than the size of each read-out electrode 21. Electrodes of various shapes can be used as the reference electrodes 22. FIG. 2A illustrates an example in which the reference electrodes 22 each have a square electrode shape.

From the correspondence relation with FIG. 1, FIG. 2A illustrates an example in which each reference electrode 22 is arranged in such a manner that nine read-out electrodes 21, i.e., three read-out electrodes 21 in the row direction X three read-out electrodes 21 in the column direction, are arranged. One reference electrode 22 includes nine opening portions 22A located at positions respectively corresponding to the nine read-out electrodes 21 arranged in a matrix shape within the plane of the reference electrode. Further, in each reference electrode 22, nine read-out electrodes 21, which are arranged in a matrix shape, are respectively located in the nine opening portions 22A. In other words, the read-out electrodes 21 are arranged so as to be located within the respective opening portions 22A in each of the reference electrodes 22.

The electrode layout of the read-out electrodes 21 and the reference electrodes 22 as illustrated in FIG. 2A is suitable for reading out a local potential change. For example, to read out the action potential of a living cell having a size of about 5 [μm], the read-out electrodes 21 each having an electrode size of about 5 [μm] and the reference electrodes 22 having a size that is 10 times or more the size of the read-out electrodes, that is, 50 [μm] or more are arranged.

In this case, an action potential generation portion is equivalent to one local point. A potential variation in the reference electrode 22 having a size of 50 [μm] is about 10 times that in the read-out electrode 21 having a size of 5 [μm]. In addition, the action potential of a living cell can be measured by taking the difference between the potential detected by each of the read-out electrodes 21 and the potential detected by each of the reference electrodes 22.

Figure 2B:
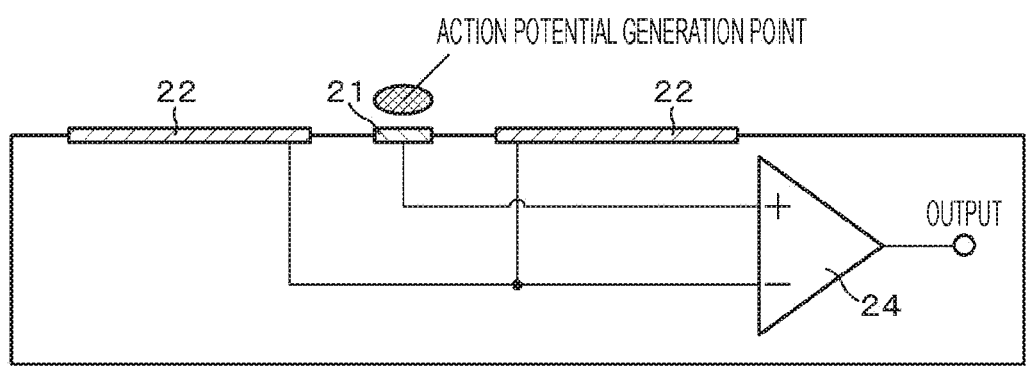
FIG. 2B is a schematic view illustrating an example of a wiring structure between each of read-out electrodes and a reference electrode and a differential amplifier.

FIG. 2B illustrates an example of wiring between each of the read-out electrodes 21 and the reference electrode 22 and one differential amplifier of the amplification units 14A and 14B. As described above, with the configuration in which the reference electrodes 22 are arranged in the vicinity of the read-out electrodes 21, more specifically, within the array of the read-out electrodes 21, the position of each read-out electrode 21 and the position of each reference electrode 22 can be located at a substantially equal distance from the position of a differential amplifier 24. With this configuration, two wires for connecting each read-out electrode 21 and each reference electrode 22 to two input terminals of the corresponding differential amplifier 24 have an approximately electrically equivalent wiring capacitance and capacitance with environment, and thus noise superimposed on one of these wires can be made equal to noise superimposed on the other one of these wires. Accordingly, noise included in the output from the differential amplifier 24 when the difference is taken can be suppressed.

Embodiment 2

Figure 3:
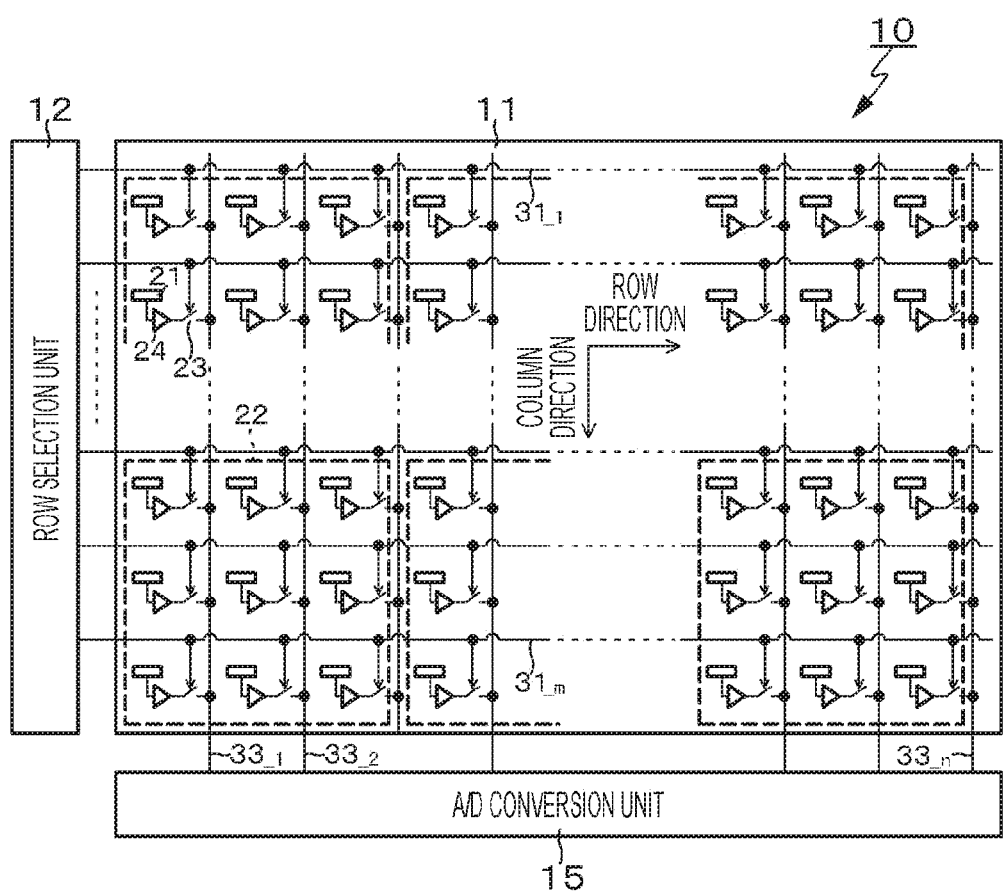
FIG. 3 is a configuration diagram schematically illustrating a configuration of a potential measurement device according to Embodiment 2.

Embodiment 2 is a modified example of Embodiment 1. FIG. 3 schematically illustrates a configuration of a potential measurement device according to Embodiment 2. The potential measurement device 10 according to Embodiment 1 has a configuration in which a plurality of differential amplifiers 24 of the amplification units 14A and 14B is commonly provided for the plurality of read-out electrodes 21 arranged in an array shape. On the other hand, the potential measurement device 10 according to Embodiment 2 has a configuration in which the differential amplifiers 24 are respectively provided for the plurality of read-out electrodes 21 arranged in an array shape.

Further, in each of the plurality of read-out electrodes 21, the switches 23 are each provided between the output end of the corresponding differential amplifier 24 and the corresponding one of the signal read-out lines $33_1$ to $33_n$. Each switch 23 is driven to be turned on by the row selection signal applied from the row selection unit 12 via the row selection lines $31_1$ to $31_m$. With this configuration, the potential detected by each read-out electrode 21 is output to the signal read-out lines $33_1$ to $33_n$ via the corresponding differential amplifier 24 and the corresponding switch 23, and is transmitted to an A/D converter 15 through the signal read-out lines $33_1$ to $33_n$.

Note that, for simplification of the drawings, FIG. 3 illustrates that only the detection potential of each read-out electrode 21 is supplied to the differential amplifier 24. However, the detection potential of each of the reference electrodes 22 to which the respective read-out electrodes 21 belong is also supplied. Further, in each differential amplifier 24, the difference between the detection potentials of the electrodes 21 and 22 is taken. The difference obtained by the differential amplifier 24 is sequentially read out for each row under the driving of the row selection unit 12. The A/D conversion unit 15 performs A/D conversion on the difference and outputs a digital value corresponding to the potential detected by the read-out electrodes 21.

Embodiment 3

Figure 4:
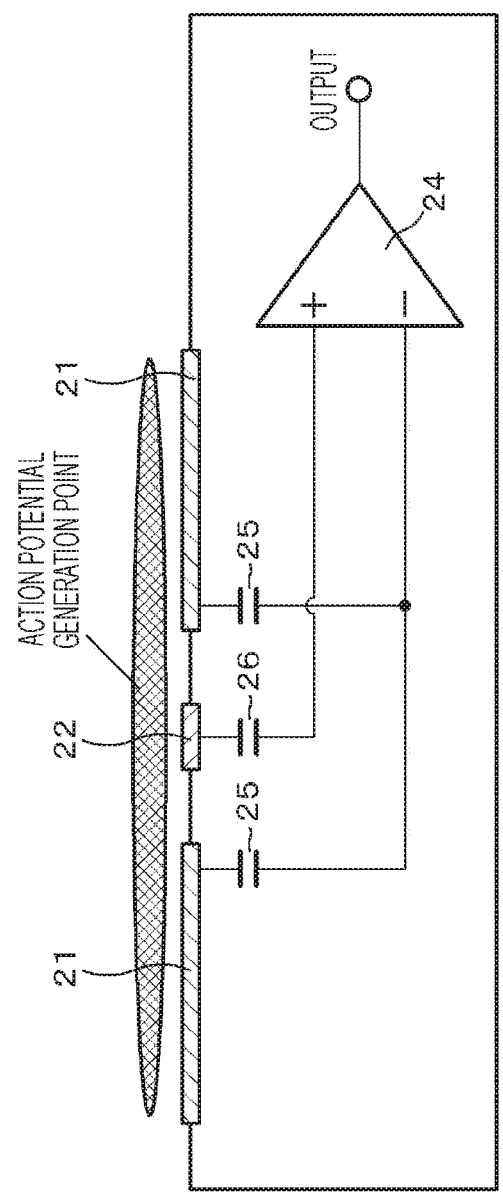
FIG. 4 is a schematic view illustrating an example of a wiring structure between each of read-out electrodes and a reference electrode and a differential amplifier in a potential measurement device according to Embodiment 3.

Embodiment 3 is a modified example of Embodiment 1. FIG. 4 illustrates a wiring structure between each of the read-out electrodes 21 and the reference electrode 22 and the differential amplifier 24 in a potential measurement device according to Embodiment 3. Embodiment 1 has a configuration in which the electrode size of each reference electrode 22 is set to be larger than the electrode size of each read-out electrode (see FIG. 2A). On the other hand, Embodiment 3 has a configuration in which the electrode size of each reference electrode 22 is set to be smaller than the electrode size of each read-out electrode 21.

Such an electrode layout example is suitable for cases where the size of a cell is approximately the same as the size of each read-out electrode, or the size of a cell is larger than the size of each read-out electrode. In such cases, electric charge uniformly reaches the entire area of each electrode, so that the amount of electric charge is in proportion to the size of the electrode. In addition, the wiring structure according to this embodiment has a configuration in which potential conversion capacitances 25 and a potential conversion capacitance 26 are connected in series between each of the read-out electrode 21 and the reference electrode 22 and two input terminals of the differential amplifier 24.

Assume herein that each read-out electrode 21 has an area (electrode size) and electrode capacitance that are A times those of the reference electrode 22. Also assume that the potential conversion capacitances 25 and 26 have the same capacitance value. The phrase "same capacitance value" used herein indicates not only a case were the capacitance values are exactly the same, but also a case where the capacitance values are substantially the same. The presence of various variations caused in design or production is allowed. In addition, a gate capacitance of a transistor connected for reading out the potential may be used.

Assume herein that the capacitance value of each reference electrode 22 is represented by C, the amount of electric charge input to each reference electrode 22 is represented by Q, and the capacitance value of the potential conversion capacitance 26 is represented by C', a potential difference $\Delta V_2$ generated between the reference electrode 22 and the potential conversion capacitance 26 is expressed as follows.

$$\Delta V_1 = Q(1/C + 1/C') \qquad (1)$$

On the other hand, a potential difference $\Delta V_1$ generated between the read-out electrode 21 and the potential conversion capacitance 25 is expressed as follows.

$$\Delta V_1 = Q(1/C + A/C') \qquad (2)$$

The potential generated in the read-out electrode 21 is larger than the potential generated in the reference electrode 22.

If the capacitance value of each of the potential conversion capacitance 25 and the potential conversion capacitance 26 is smaller, and preferably, sufficiently smaller than the capacitance value (capacitance value between an electrode and solvent) of each of the read-out electrode 21 and the reference electrode 22, the potential difference is in proportion to the area of the electrode. It is known that, for example, when the area of the read-out electrode 21 is 20 [μm] and the area of the reference electrode 22 is 1 [μm], the electrode capacitance is about several [pF]. On the other hand, for example, assuming that gate capacitances of transistors connected for reading out a potential are respectively represented by the potential conversion capacitances 25 and 26, the electrode capacitance is about several [fF]. Accordingly, the potential generated in the read-out electrode 21 is equal to an area ratio, i.e., 400 times that of the potential generated in the reference electrode 22.

Embodiment 4

Figure 5:
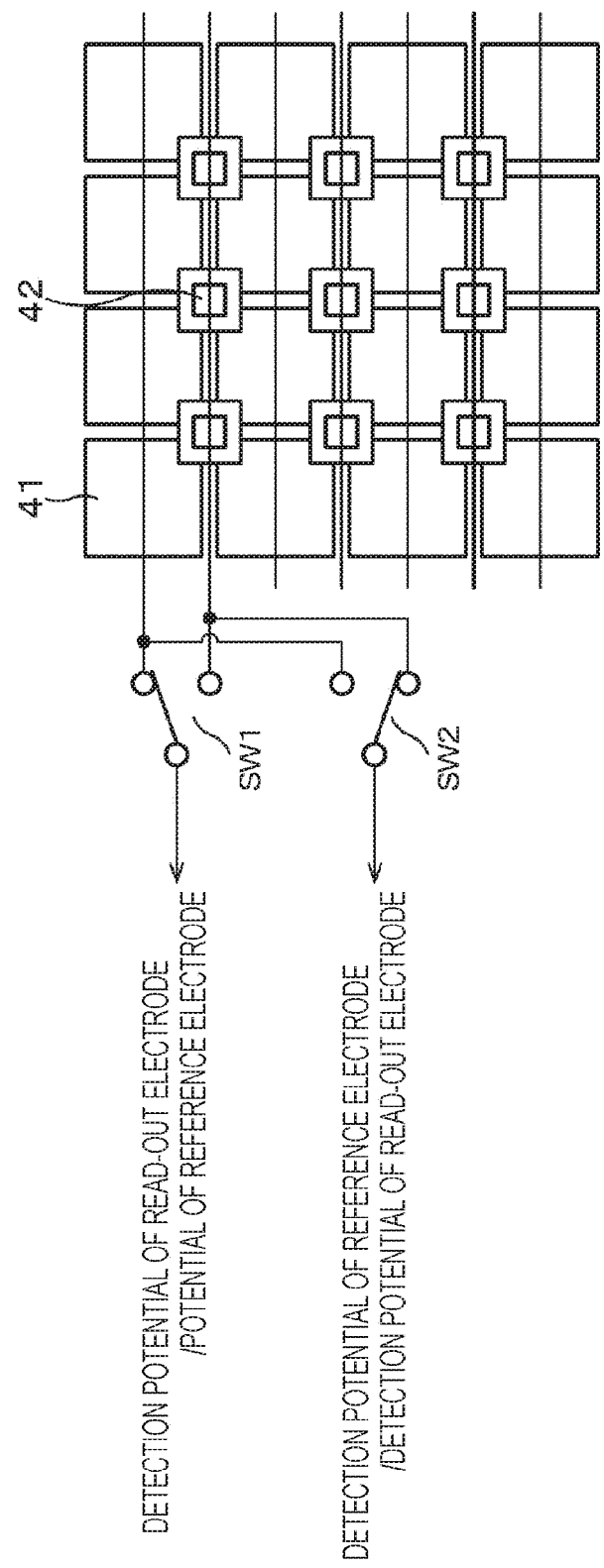
FIG. 5 is a schematic view schematically illustrating a configuration of a potential measurement device according to Embodiment 4.

Embodiment 4 is a modified example of Embodiment 1 and Embodiment 3. FIG. 5 schematically illustrates a configuration of a potential measurement device according to Embodiment 4. As illustrated in FIG. 5, the potential measurement device according to this embodiment includes first and second electrodes having different electrode sizes, i.e., electrodes 41 having a relatively large electrode size (hereinafter also referred to simply as "large electrodes 41"), and electrodes 42 having a relatively small electrode size (hereinafter also referred to simply as "small electrodes 42"). Further, the potential measurement device according to this embodiment has a device configuration in which the large electrodes 41 and the small electrodes 42 are arranged in an array shape, a differential amplifier (see FIG. 3) is provided for each electrode, and an average value is taken on the analog output or data obtained after A/D conversion.

As for the relationship between the size of each large electrode 41 and the size of each small electrode 42, for example, the relationship between the read-out electrode 21 and the reference electrode 22 in Embodiment 1 (see FIG. 2A), or the relationship between the read-out electrode 21 and the reference electrode 22 in Embodiment 3 (see FIG. 4) can be employed. Further, in the potential measurement device according to this embodiment, the large electrodes 41 and the small electrodes 42 are used differently depending on the intended use of measurement.

Specifically, like in the case of Embodiment 1, the small electrodes 42 are used as the read-out electrodes 21, and the large electrodes 41 are used as the reference electrodes 22. Further, the detection potential of each of the small electrodes 42 is used as the detection potential at the action potential generation point, while a plurality of large electrodes 41 is grouped and an average of the detection potentials of the plurality of electrodes 41 is taken and the average value is used as the reference potential. This example is suitable for the measurement to read out a local potential change.

Alternatively, like in the case of Embodiment 3, the large electrodes 41 are used as the read-out electrodes 21 and the small electrodes 42 are used as the reference electrodes 22. Further, a plurality of small electrodes 42 is grouped and an average of the detection potentials of the plurality of electrodes 42 is taken, and the average value is used as the reference potential. Meanwhile, small electrodes 42 other than the plurality of small electrodes 42 and the large electrodes 41 are grouped and an average of the detection potentials of these electrodes is taken, and the average value is used as the detection potential at the action potential generation point. This example is suitable for cases where the size of a cell is approximately the same as the size of each read-out electrode 21, or the size of a cell is larger than the size of each read-out electrode 21.

The use of the former example and the latter example differently can be achieved by switching two switches SW1 and SW2, which are provided for each row, for example, as schematically illustrated in FIG. 5. Note that, for simplification of the drawings, FIG. 5 illustrates only two switches SW1 and SW2 in a first row. The two switches SW1 and SW2 work in conjunction. Further, when the switch SW1 selects the detection potential of the large electrode 41 in the first row as the detection potential of the reference electrode 22, the switch SW2 selects the detection potential of the small electrode 42 in the first row as the detection potential of the read-out electrode 21. On the contrary, when the switch SW1 selects the detection potential of the small electrode 42 in the first row as the detection potential of the reference electrode 22, the switch SW2 selects the detection potential of the large electrode 41 in the first row as the detection potential of the read-out electrode 21.

As a modified example of Embodiment 4, the following configuration can also be employed. That is, the large electrode (first electrode) 41 and the small electrode (second electrode) 42 are configured using a combination of fine electrodes so that a large number of fine electrodes having a constant size can be arranged in an array shape and an area difference as described above in Embodiment 1 and Embodiment 3 can be achieved. The electrode size of each fine electrode is not limited, but is smaller, and preferably, sufficiently smaller than the size (e.g., about 5 [μm]) of a living cell.

Figure 6:
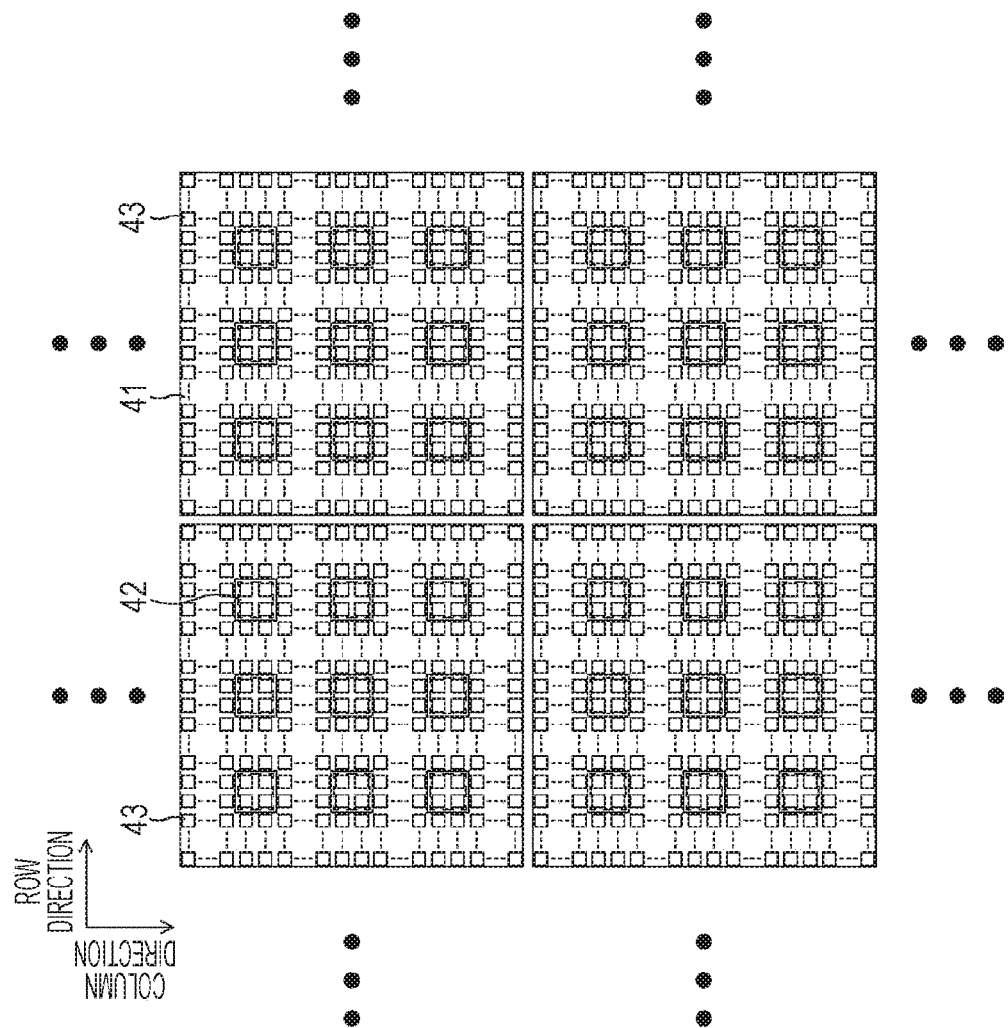
FIG. 6 is an electrode layout diagram illustrating an array of fine electrodes according to a modified example of Embodiment 4, and a relationship between large electrodes and small electrodes.

Specifically, for example, the correspondence relation with FIG. 2A is described by way of example. As illustrated in FIG. 6, in an array of fine electrodes 43, several fine electrodes 43 are grouped and used as the small electrode 42, and several hundred or more fine electrodes 43 are grouped and used as the large electrode 41. In the case of this example, in the correspondence with FIG. 2A, the small electrodes 42 are used as the read-out electrodes 21, and the large electrodes 41 are used as the reference electrodes 22. Further, an average value of the detection potentials of several fine electrodes 43 constituting the small electrode 42 is used as the detection potential of the small electrode 42, and an average value of the detection potentials of several hundred or more fine electrodes 43 constituting the large electrode 41 is used as the detection potential of the large electrodes 41.

Embodiment 5

Figure 7:
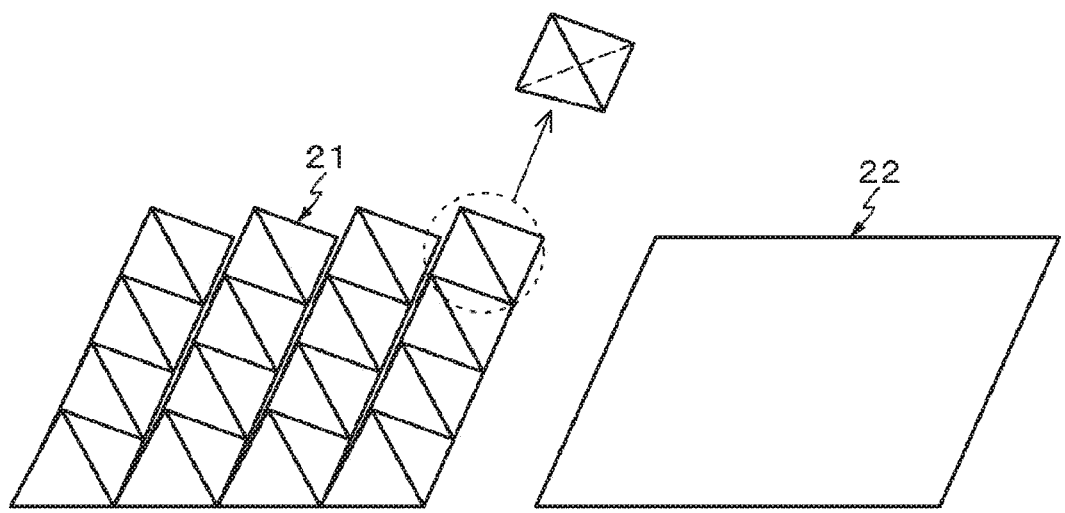
FIG. 7 is a schematic perspective view illustrating an example of an electrode structure of read-out electrodes in a potential measurement device according to Embodiment 5.

Embodiment 5 is a modified example of Embodiment 1. FIG. 7 illustrates an example of the electrode structure of the read-out electrodes 21 in a potential measurement device according to Embodiment 5. The electrode structure of each read-out electrode 21 is a planar structure in Embodiment 1, while in this embodiment, a three-dimensional structure is employed. Specifically, in this embodiment, a three-dimensional structure is used as the electrode structure of the read-out electrodes 21, thereby increasing the surface area as compared with a case where a planar structure is employed. On the other hand, a planar structure is used as the electrode structure of the reference electrodes 22, like in the case of Embodiment 1.

In this manner, a three-dimensional structure is used as the electrode structure of the read-out electrodes 21 and a planar structure is used as the electrode structure of the reference electrodes 22, thereby making it possible to increase the surface area ratio between each read-out electrode 21 and each reference electrode 22 as compared with a case where a planar structure is used as the electrode structure of each of the read-out electrodes 21 and the reference electrodes 22 (Embodiment 1). As is obvious from the above description, when the surface area ratio between each read-out electrode 21 and each reference electrode 22 is large, the difference between the potential detected by each read-out electrode 21 and the potential detected by each reference electrode 22 can be increased.

FIG. 7 illustrates a triangular pyramid structure as the three-dimensional structure of the read-out electrodes 21. However, the electrode structure is not limited to the triangular pyramid structure. Any structure, such as a quadrangular pyramid structure, a cubic structure, or a spherical structure, can be employed as long as the structure is capable of increasing the surface area as compared with a planar structure.

Examples of a method for forming the three-dimensional structure for increasing the surface area include a plating method using platinum black, a method of forming a hole or a pyramid-shaped nanostructure by etching, self aligning, or the like, and a method of attaching a carbon nanotube (CNT), a nanowire, a quantum dot, or the like to an electrode.

Note that the present disclosure can also have the following configurations.

[1] A potential measurement device including:
a plurality of read-out electrodes arranged in an array shape and configured to detect a potential at an action potential generation point generated due to a chemical change;
a reference electrode configured to detect a reference potential; and
an amplification unit configured to obtain a potential difference between a detection potential detected by each of the read-out electrodes and a detection potential detected by the reference electrode,
in which the reference electrode is arranged within the array of the read-out electrodes.

[2] The potential measurement device according to [1], in which the read-out electrodes, the reference electrode, and the amplifier are integrated on one semiconductor substrate.

[3] The potential measurement device according to [1] or [2], in which an electrode size of the reference electrode is larger than the electrode size of each of the read-out electrodes.

[4] The potential measurement device according to any of [1] to [3], in which the read-out electrodes each have an electrode size substantially equal to a size of the action potential generation point.

[5] The potential measurement device according to [3] or [4], in which
the reference electrode includes a plurality of opening portions within a plane of the reference electrode, and
the read-out electrodes are arranged in such a manner that the read-out electrodes are respectively located within the opening portions of the reference electrode.

[6] The potential measurement device according to any of [1] to [5], including an A/D conversion unit configured to perform A/D conversion of an output from the amplifier, the A/D conversion unit being formed on a semiconductor substrate on which the read-out electrodes, the reference electrode, and the amplifier are formed.

[7] The potential measurement device according to any of [1] to [6], in which
the amplification unit includes a plurality of differential amplifiers, and
the plurality of differential amplifiers is commonly provided for the plurality of read-out electrodes.

[8] The potential measurement device according to any of [1] to [6], in which
the amplification unit includes a plurality of differential amplifiers, and
the plurality of differential amplifiers is respectively provided for the plurality of read-out electrodes.

[9] The potential measurement device according to [1], including a first electrode having a relatively large electrode size, and a second electrode having a relatively small electrode size,
in which the potential measurement device is capable of switching between a case where the first electrode is used as the reference electrode and the second electrode is used as each of the read-out electrodes and a case where the first electrode is used as each of the read-out electrodes and the second electrode is used as the reference electrode.

[10] The potential measurement device according to [9], in which
each detection potential of the second electrode is set as a detection potential at the action potential generation point, and
a plurality of first electrodes is grouped and an average value of detection potentials of the plurality of first electrodes is set as the reference potential.

[11] The potential measurement device according to [9], in which
a plurality of second electrodes is grouped and an average value of detection potentials of the plurality of second electrodes is set as a reference potential, and
second electrodes other than the plurality of second electrodes and the first electrode are grouped and an average of detection potentials of the second electrodes other than the plurality of second electrodes and the first electrode is taken, and the average value is set as a detection potential at the action potential generation point.

[12] The potential measurement device according to [9], in which
a large number of fine electrodes are arranged in an array shape,
an average value of detection potentials of several fine electrodes is set as a detection potential of the second electrode, and an average value of detection potentials of several hundred or more fine electrodes is set as a detection potential of the first electrode.

[13] The potential measurement device according to [1], in which in a case where an electrode size of each of the read-out electrodes is larger than the electrode size of the reference electrode,
potential conversion capacitances having the same capacitance value are connected in series between the amplification unit and each of the read-out electrodes and the reference electrode, and
a capacitance value of each of the potential conversion capacitances is smaller than an electrode-to-solvent capacitance value of each of the read-out electrodes and the reference electrode.

[14] The potential measurement device according to [1], in which an electrode structure of each of the read-out electrodes and the reference electrode is a planar structure.

[15] The potential measurement device according to [1], in which
an electrode structure of the reference electrode is a planar structure, and
an electrode structure of each of the read-out electrodes is a three-dimensional structure.

REFERENCE SIGNS LIST 10 potential measurement device
11 electrode unit
12 row selection unit
13 column selection unit
14A, 14B amplification unit
15, 15A, 15B A/D conversion unit
16 semiconductor substrate (semiconductor chip)
21 read-out electrode
22 reference electrode
23 switch
24 differential amplifier
25, 26 potential conversion capacitance
$31_1$-$31_m$ row selection line
$32_1$-$32_n$ column selection line
41 first electrode (large electrode)
42 second electrode (small electrode)
43 fine electrode

The invention claimed is:

1. A potential measurement device, comprising:
a first analog to digital (A/D) conversion unit on a first side of a semiconductor substrate;
a second A/D conversion unit on a second side of the semiconductor substrate;
a plurality of differential amplifiers, wherein
a first set of differential amplifiers of the plurality of differential amplifiers is on the first side of the semiconductor substrate,
a second set of differential amplifiers of the plurality of differential amplifiers is on the second side of the semiconductor substrate, and
the first set of differential amplifiers is different from the second set of differential amplifiers;
a plurality of read-out electrodes in an array, wherein
each read-out electrode of the plurality of read-out electrodes is configured to detect a potential at an action potential generation point, and
the potential is based on a chemical change;
a reference electrode configured to detect a reference potential, wherein
the plurality of differential amplifiers is configured to obtain a potential difference between the potential detected by each read-out electrode of the plurality of read-out electrodes and the reference potential detected by the reference electrode,
a first distance between each read-out electrode of the plurality of read-out electrodes and a corresponding differential amplifier of the plurality of differential amplifiers is equal to a second distance between the reference electrode and the corresponding differential amplifier,
the reference electrode is within the array of the plurality of read-out electrodes, and
the plurality of read-out electrodes and the reference electrode are between the first side of the semiconductor substrate and the second side of the semiconductor substrate; and
wherein:
the reference electrode includes a plurality of opening portions within a plane of the reference electrode, and
each read-out electrode of the plurality of read-out electrodes is within a corresponding opening portion of the plurality of opening portions of the reference electrode.

2. The potential measurement device according to claim 1, wherein a size of the reference electrode is larger than a size of each read-out electrode of the plurality of read-out electrodes.

3. The potential measurement device according to claim 1, wherein a size of each read-out electrode of the plurality of read-out electrodes is equal to a size of the action potential generation point.

4. The potential measurement device according to claim 1, wherein the first A/D conversion unit and the second A/D conversion unit are configured to execute analog to digital (A/D) conversion process on an output from the plurality of differential amplifiers.

5. The potential measurement device according to claim 1, wherein the plurality of differential amplifiers is commonly provided for the plurality of read-out electrodes.

6. The potential measurement device according to claim 1, wherein
in a case where a size of each read-out electrode of the plurality of read-out electrodes is larger than a size of the reference electrode, potential conversion capacitances having a same capacitance value are connected in series between the plurality of differential amplifiers and each read-out electrode of the plurality of read-out electrodes and the reference electrode, and
a capacitance value of each of the potential conversion capacitances is smaller than an electrode-to-solvent capacitance value of each read-out electrode of the plurality of read-out electrodes and the reference electrode.

7. The potential measurement device according to claim 1, wherein a structure of each read-out electrode of the plurality of read-out electrodes and the reference electrode is a planar structure.

8. The potential measurement device according to claim 1, wherein
a structure of the reference electrode is a planar structure, and
a structure of each read-out electrode of the plurality of read-out electrodes is a three-dimensional structure.

* * * * *